(12) United States Patent
Ben Youssef

(10) Patent No.: US 7,476,219 B2
(45) Date of Patent: Jan. 13, 2009

(54) URINARY INCONTINENCE DEVICE

(76) Inventor: Oumeima Ben Youssef, 61 May Road, Gillingham, Kent (GB) ME7 5UY ( * ) Notice: Subject to any disclaimer, the term of this patent is extended or adjusted under 35 U.S.C. 154(b) by 0 days.

(21) Appl. No.: 10/594,914

(22) PCT Filed: Mar. 31, 2005

(86) PCT No.: PCT/GB2005/001238

§ 371 (c)(1),
(2), (4) Date: Sep. 29, 2006

(87) PCT Pub. No.: WO2005/094739

PCT Pub. Date: Oct. 13, 2005

(65) Prior Publication Data

US 2007/0142793 A1    Jun. 21, 2007

(30) Foreign Application Priority Data

Mar. 31, 2004    (GB) ................... 0407317.7

(51) Int. Cl.
*A61F 5/44* (2006.01)
(52) U.S. Cl. .................... 604/329; 604/79; 604/77; 604/540; 604/544; 604/317; 604/327; 604/331; 604/332; 604/346; 604/347; 604/349; 604/351; 604/353; 604/354; 604/355; 128/830
(58) Field of Classification Search .............. 604/329, 604/79, 77, 540, 544, 317, 327, 332, 331, 604/346, 347, 349, 351, 353, 354, 355; 128/830
See application file for complete search history.

(56) References Cited

U.S. PATENT DOCUMENTS 3,374,790 A * 3/1968 Mayhorne .............. 604/347
3,528,423 A   9/1970 Lee
3,554,184 A * 1/1971 Habib .................... 600/29
3,661,155 A   5/1972 Lidan
3,776,235 A   12/1973 Ratcliffe et al.

(Continued)

FOREIGN PATENT DOCUMENTS

DE    296 18 121    2/1997

(Continued)

OTHER PUBLICATIONS

PCT International Search Report, PCT/GB2005/001238, mailed Nov. 7, 2005.

(Continued)

*Primary Examiner*—Tatyana Zalukaeva
*Assistant Examiner*—Ilya Y Treyger
(74) *Attorney, Agent, or Firm*—Myers, Bigel, Sibley & Sajovec, P.A.

(57) ABSTRACT

The invention relates to an external female incontinence device. The device comprises a flexible elastic strip having an opening in the strip, a fluid collection means surrounding the opening on one face, the strip and opening are sized and shaped so that when stretch fitted over the external urogenital organs the labia minor extends through the opening and a fluid tight fit between the upper face of the strip and the flesh surrounding the labia minora is formed. The device may further comprise a waistband for attachment of the device and to assist in maintaining a positive tension to press the device against the flesh surrounding the labia minora.

19 Claims, 6 Drawing Sheets

U.S. PATENT DOCUMENTS

| | | | |
|---|---|---|---|
| 3,995,329 A | 12/1976 | Williams | |
| 4,019,498 A | 4/1977 | Hawtrey et al. | |
| 4,198,979 A | 4/1980 | Cooney et al. | |
| 4,457,314 A | 7/1984 | Knowles et al. | |
| 4,692,160 A | 9/1987 | Nussbaumer | |
| 4,822,347 A | 4/1989 | MacDougall | |
| 4,846,819 A | 7/1989 | Welch | |
| 4,889,533 A | 12/1989 | Beecher | |
| 4,967,767 A * | 11/1990 | Harris et al. | 128/844 |
| 5,053,027 A | 10/1991 | Manfredi et al. | |
| 5,267,988 A * | 12/1993 | Farkas | 604/329 |
| 5,411,495 A | 5/1995 | Willingham et al. | |
| 5,785,640 A | 7/1998 | Keresch et al. | |
| 5,893,176 A | 4/1999 | Magiera et al. | |
| 6,149,635 A * | 11/2000 | Tuckey | 604/329 |
| 6,505,355 B1 | 1/2003 | Mutke | |

FOREIGN PATENT DOCUMENTS

| | | |
|---|---|---|
| DE | 29618121 | 2/1997 |
| GB | 2090144 A | 7/1982 |
| GB | 2126902 A | 9/1982 |
| GB | 2126902 A | 4/1984 |
| GB | 2129686 A | 5/1984 |
| GB | 2193438 A | 8/1985 |
| GB | 2193438 A | 2/1988 |

OTHER PUBLICATIONS

International Search Report and the Written Opinion, date of mailing Oct. 12, 2006 for corresponding PCT application No. PCT/GB2005/001238 (8 pages).

* cited by examiner

URINARY INCONTINENCE DEVICE

RELATED APPLICATIONS

This application is a national stage application of PCT/GB2005/001238, filed Mar. 31, 2005, which claims priority to United Kingdom Application No. GB 0407317.7, filed Mar. 31, 2004, the contents of the above applications are hereby incorporated by reference as if recited in full herein.

The present invention relates to a female incontinence device, in particular an external incontinence device.

Due to the anatomy of the female external urogenital organs, the management of incontinence in female patients has always been difficult both in terms of preventing leakage and acceptability for the patient. There have been a number of devices for female incontinence that attempt to secure an effective seal in a number of ways. Some devices provide an intra vaginal structure to support the device in place. Examples of such devices include those described in U.S. Pat. No. 3,776,235 (Ratcliffe et al), U.S. Pat. No. 3,661,155 (Linden), U.S. Pat. No. 4,198,979 (Cooney et al), U.S. Pat. No. 4,019,498 (Hawtrey et al), U.S. Pat. No. 5,785,640 (Keresch et al) and UK patent applications GB 2126902A and GB 2090144A. However, such devices have been found to be rigid, uncomfortable, intrusive and still prone to leakage.

Other devices have used an external adhesive in an attempt to seal the device to the patient's skin and avoid leakage. Examples of such devices include U.S. Pat. No. 4,822,347 (MacDougal) and UK applications GB 2129686A and GB 2193438A. These devices have also proven to be ineffective in providing an effective seal, particularly with mobile patients.

Further devices include U.S. Pat. No. 4,846,819 (Welch) which employs a deformable polymer gel ring to provide a seal. The use of a sealing pad of foam plastic material is described in U.S. Pat. No. 3,374,790 (Mayhorne) but again these devices have been found to be ineffective in preventing leakage.

Other devices provide a contact seal with the patient between the labia minora and labia majora. These devices include U.S. Pat. No. 4,889,533 (Beecher) which includes a pessary for insertion into the vagina to keep the device in place, an elevated side wall around the labia minora and flanges that engage the labia majora. The device requires a flexible crotch panel that is attached to a waistband through straps. Such a device is uncomfortable due to vaginal insertion and engagement of the labia majora. U.S. Pat. No. 3,995,329 (Williams) describes a hand held urine collection device for use in a standing position designed to be held and pressed against labia majora and has elevated side walls of limited resilience such that when hand pressure is applied by the used the flesh in contact causes abutted flesh to yield to conform to the device to form a seal. The device is not designed for continuous wear and is not suitable for incontinent patients. U.S. Pat. No. 5,893,176 (Magiera et al) describes a hand held device for urine collection whilst in the standing position, the device includes two sealing rings, the interior ring comprises a circumferential wall which engages the exterior of the labia minor and a exterior ring which engages the exterior of the labia majora. The device is intended to be hand held to allow a female user to urinate in a standing position and is not suitable for use in an incontinent person. Such devices include an elevated ring structure to engage the labia minora and an exterior wall or flanges to engage and press on the labia majora to keep the device in place and obtain a contact seal. However, it is found that pressing against the exterior of the labia majora to make a seal is uncomfortable and restrict patient movement and for an active patient such devices are prone to move and rub the patient's skin causing further discomfort.

There remains a need for a female incontinence device that can readily conform to female body shape and can provide an effective seal for both mobile and immobile patients whilst remaining comfortable for the patient without intruding into the vagina, anus, meatus or the exterior of the labia majora. The present invention overcomes these problems by providing a non-intrusive female incontinence device that utilises a flexible strip which has a substantially flat and smooth face in contact with, and forms a seal about, the female external urogenital organs. Accordingly the present invention provides, a female urinary incontinence device comprising a flexible strip having an upper face and a lower face, an opening being provided in the strip communicating between the upper and lower faces, the upper face being substantially flat, a fluid collection means affixed to the lower face of the strip in a fluid tight manner around the opening in the strip and outlet for conveying fluid away from the collection means, the device further comprising means for attaching the device to a support means, wherein the strip and opening are sized and shaped such that when it is stretch fitted over the external urogenital organs the labia minora extends through the opening and a fluid tight fit between the upper face of the strip and the flesh surrounding the base of the labia minora is formed, such that in use urine is conveyed from the urethra, through the labia minora, and into the collection means without leakage.

The flexible strip may be constructed of any suitable material having a degree of elasticity and flexibility to maintain a fluid seal during use. Suitable materials include elastomeric materials such as silicone or latex rubbers. Preferably, the material is hypoallergenic.

The opening in the strip is preferably of a substantially oval shape to assist in maintaining a seal about the labia minora. The strip in the region of the opening may also have a substantially oval shape.

The device further comprises a fluid collection means which surrounds the opening on the lower face of the strip in a fluid tight manner. Preferably, at least the portion of the collection means immediately adjacent the lower face is comprised of the same material as the strip. The collection means, or the portion adjacent the lower face and surrounding the opening, can be affixed to the lower face of the device by for example heat welding or by an adhesive but preferably it is formed integrally with the strip. In a preferred embodiment, the collection device comprises an oval cup portion surrounding the opening and formed integrally with the strip and of the same material. A second portion of the cup is separated by a thin resilient inner wall also having an opening therein and separating the first portion of the cup from the second portion which comprises a hard shell narrowing to an outlet toward its lower end which may be attached to a tube for draining urine or other fluid discharge to a storage vessel for subsequent disposal. The interior wall prevents or reduces backflow of discharged fluid, particularly if the user is in a lying position. In a preferred embodiment the collection means comprises a double walled structure, comprising an inner wall open at its lower end and an outer wall spaced from the inner wall so as to define a cavity between the two walls in which any urine that has not been discharged through the drainage outlet provided in the outer wall is collected and prevented from flowing back into the open end of the inner wall.

The device may be in the form of integral incontinence pants. Attachment means such as Velcro fasteners can be provided to allow for positioning of the device. Preferably the device is in a two part form, the first part comprising the strip and collection means provided with connection means for connection to a support means. The connection means may comprise a plurality of straps that can be connected to straps or tensioning means attached to a waistband. Preferably the connection means between the strap portion and the connections on the support means can be adjusted to maintain a positive tension so as provide a force urging the inner face of the strap against the flesh surrounding the labia minora which helps to maintain a fluid tight seal. The strap portion can for example be connected to the support means by a number of elastic straps.

In a preferred embodiment the flexible strip is bifurcated at the front and rear so as to provide a pair of anterior suspension straps and a pair of posterior suspension straps. The straps are connected to a waistband and can be adjusted to provide an optimum degree of tension so as to maintain an effective seal between flat upper face of the flexible strip and the flesh surrounding the labia minora whilst remaining comfortable for the user.

Preferably the device can be disconnected from the support means so that another can be fitted. The device can then be sterilized for reuse which can provide a considerable cost saving over disposable devices.

The device is comfortable for long term wear, it is non-intrusive in that it does not include any internal support structure such as a vaginal or urethral insertion to hold the device in place and it does not rely on exerting pressure against the exterior of the labia majora to force the labia majora to provide a seal. The device does not rely on adhesive or contact sensitive areas such as the vaginal or urethral orifice (meatus). The device can be used for permanently immobilised patients but due to the efficient sealing provided by the flexible elastomeric material the device is also suitable for mobile patients. The device is also much easier for hospital staff to change than devices which require vaginal insertion or catherisation and avoids the possible complications such as infection that can be associated with such procedures. The device can also be used to collect urine from uncooperative patients such as children or those suffering from dementia The device can also be used to collect other vaginal discharge such as experienced during periods and can be used to collect and measure the amount of bleeding give the doctor an indication of the amount of blood loss.

The invention will now be described by way of example with reference to the accompanying drawings in which.

Figure 1:
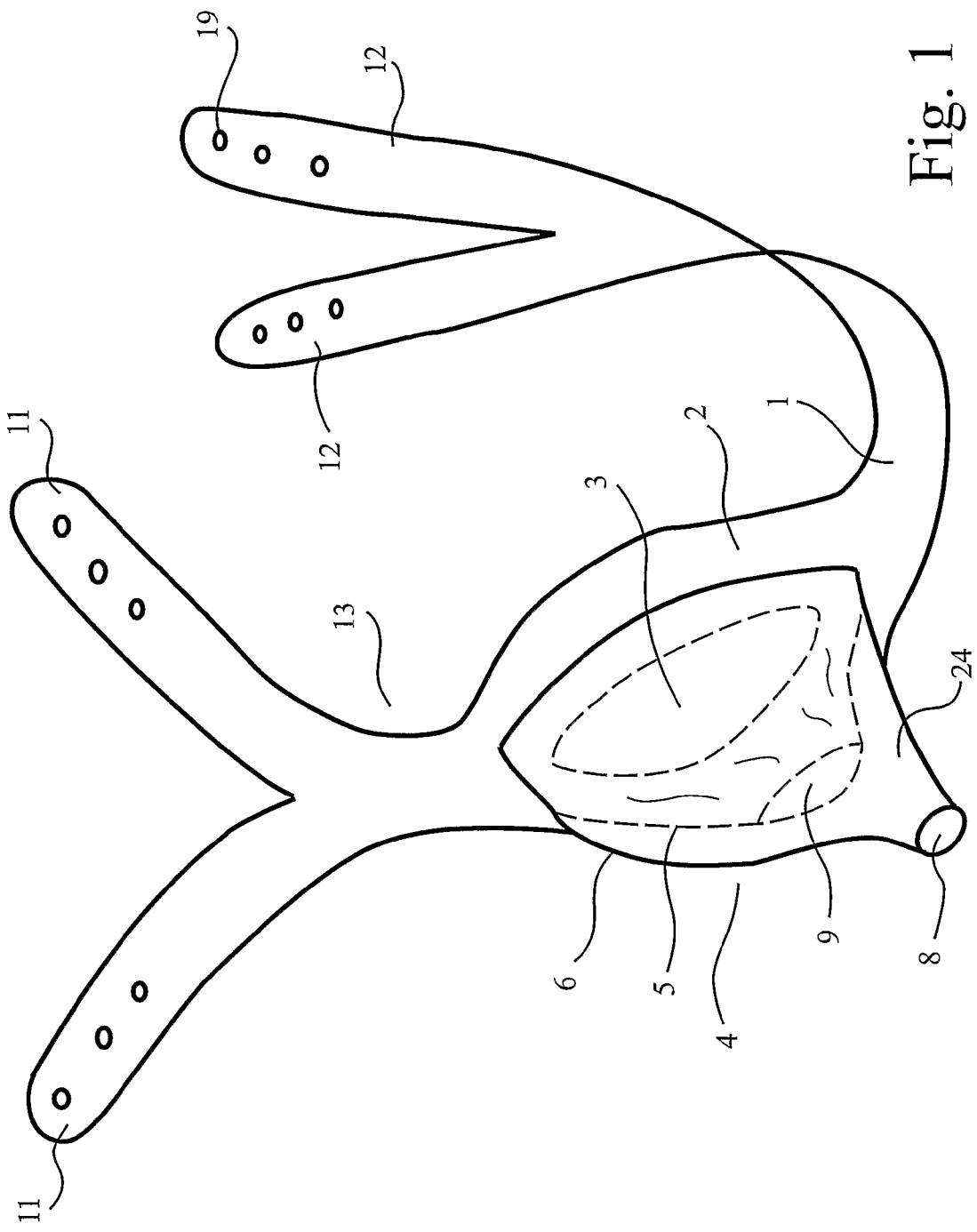
FIG. 1 is a schematic view of a urinary incontinence device according to an embodiment of the invention.
Figure 2:
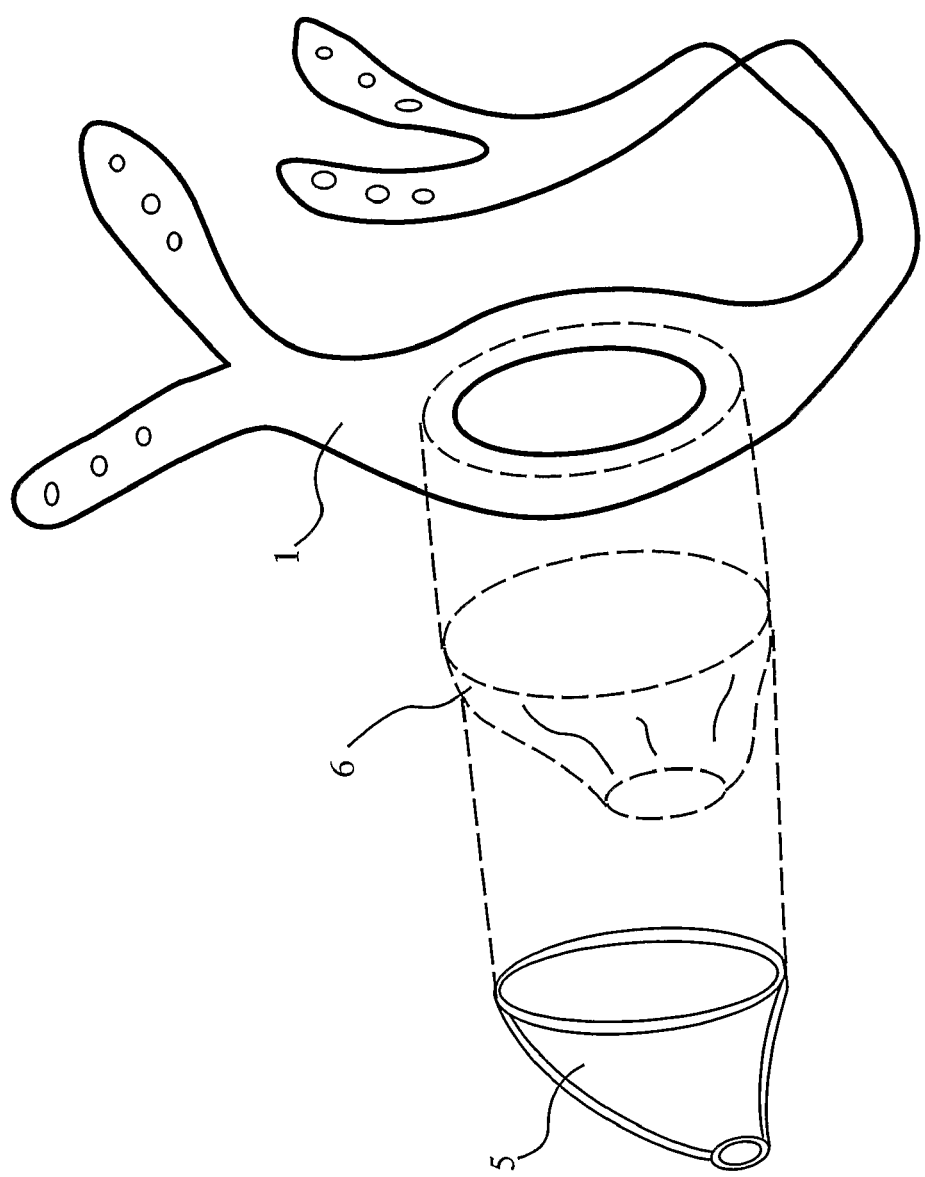
FIG. 2 is an exploded schematic view of the major components of the device of the embodiment shown in FIG. 1.

Referring to FIGS. 1 and 2, there is shown a urinary incontinence device 13 which comprises a strap part 1 made of a flexible, elastic silicon rubber material, the strap part has a substantially oval central portion 2 having an oval opening 3 therein. A fluid collection part 4 comprises a first cup portion 5 which is formed integrally with the strap part surrounding the opening on the lower face. The first cup portion is about 10 mm deep and spaced from the edge of the opening by about 3 mm. A second cup part 6 is joined to strip and surrounds the first cup part and is spaced about 10 mm from the opening. The second cup part 6 comprises 7 which is formed from the same silicone rubber material as the strip part but is thicker and accordingly more rigid and is spaced from the interior wall so as to define a cavity 24 between the inner and outer walls. The outer cup narrows at its lower end to form a tubular exit 8 that can be connected to drain to an external container. The interior wall 6 is comprised of a resilient and flexible material the same as the strap part but has relatively thin walls which are shaped so as lie against the labia minora or will tend to collapse in on themselves in parts not in contact with the labia minora. An opening 9 is provided which is in communication with the cavity 24. The strap part divides at the front and the rear to provide anterior support straps 11 and posterior support straps 12. The straps are provided with a plurality of attachment points 19 to allow for adjustment of the device.

Figure 3:
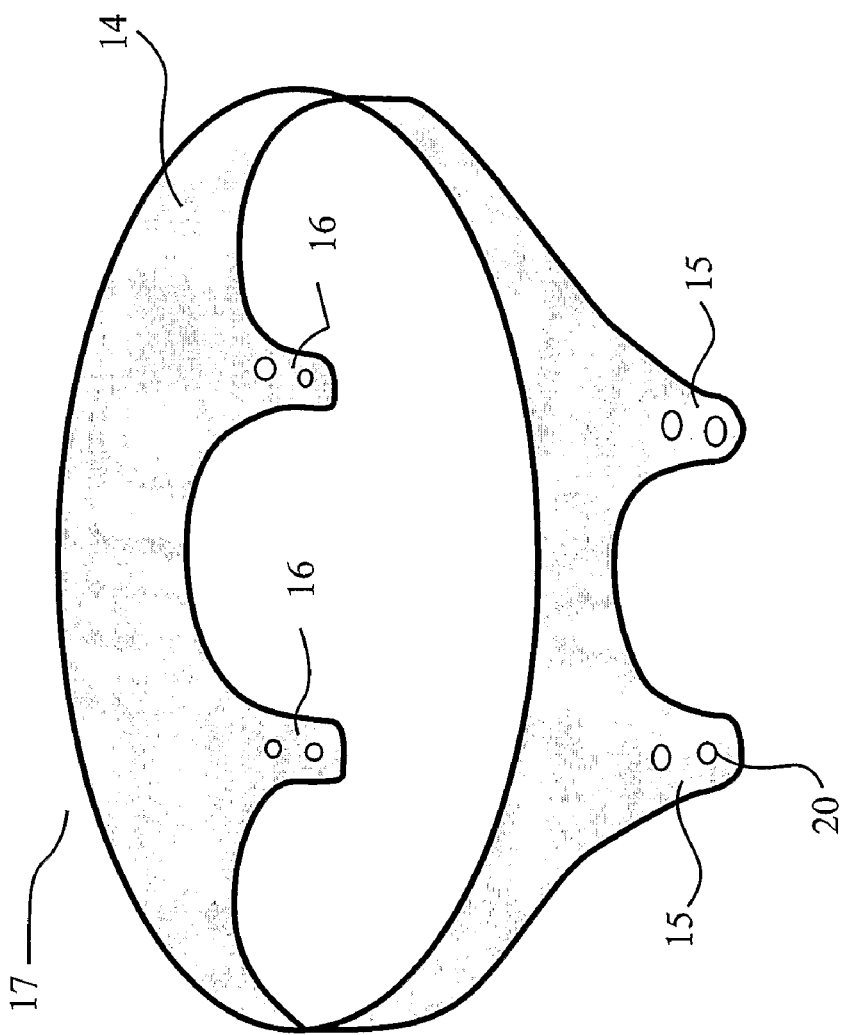
FIG. 3 is a schematic of a support harness that can be used in conjunction with the device shown in FIGS. 1 and 2.
Figure 4:
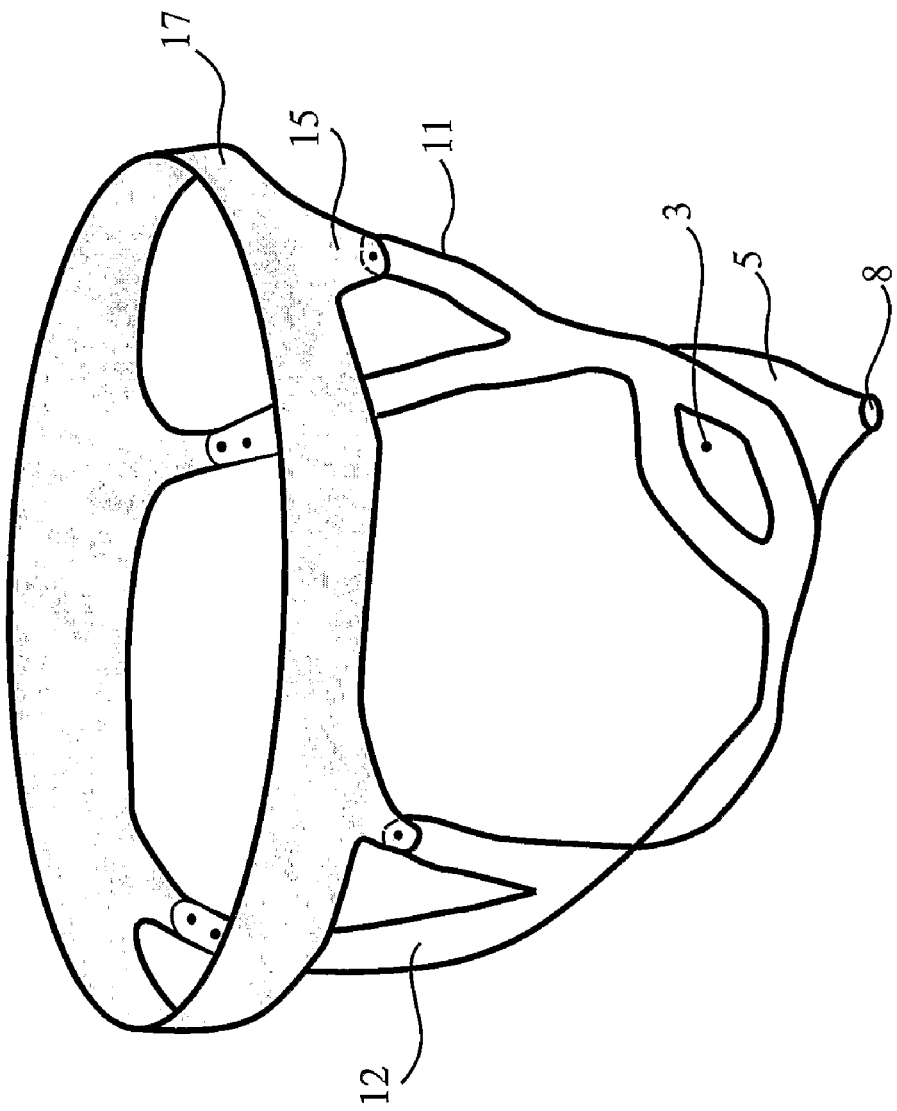
FIG. 4 shows the device of FIG. 1 attached to the support harness of FIG. 3.

Referring to FIGS. 3 and 4, in use the patient is fitted with a support harness 17 comprising a waistband 14 having front support straps 15 and rear support straps 16 attached to the waistband. The front 11 or rear 12 support straps of the incontinence device can be attached by the attachment points 19 to the corresponding front 15 or rear 16 support straps of the harness by the attachment points 20.

Figure 5:
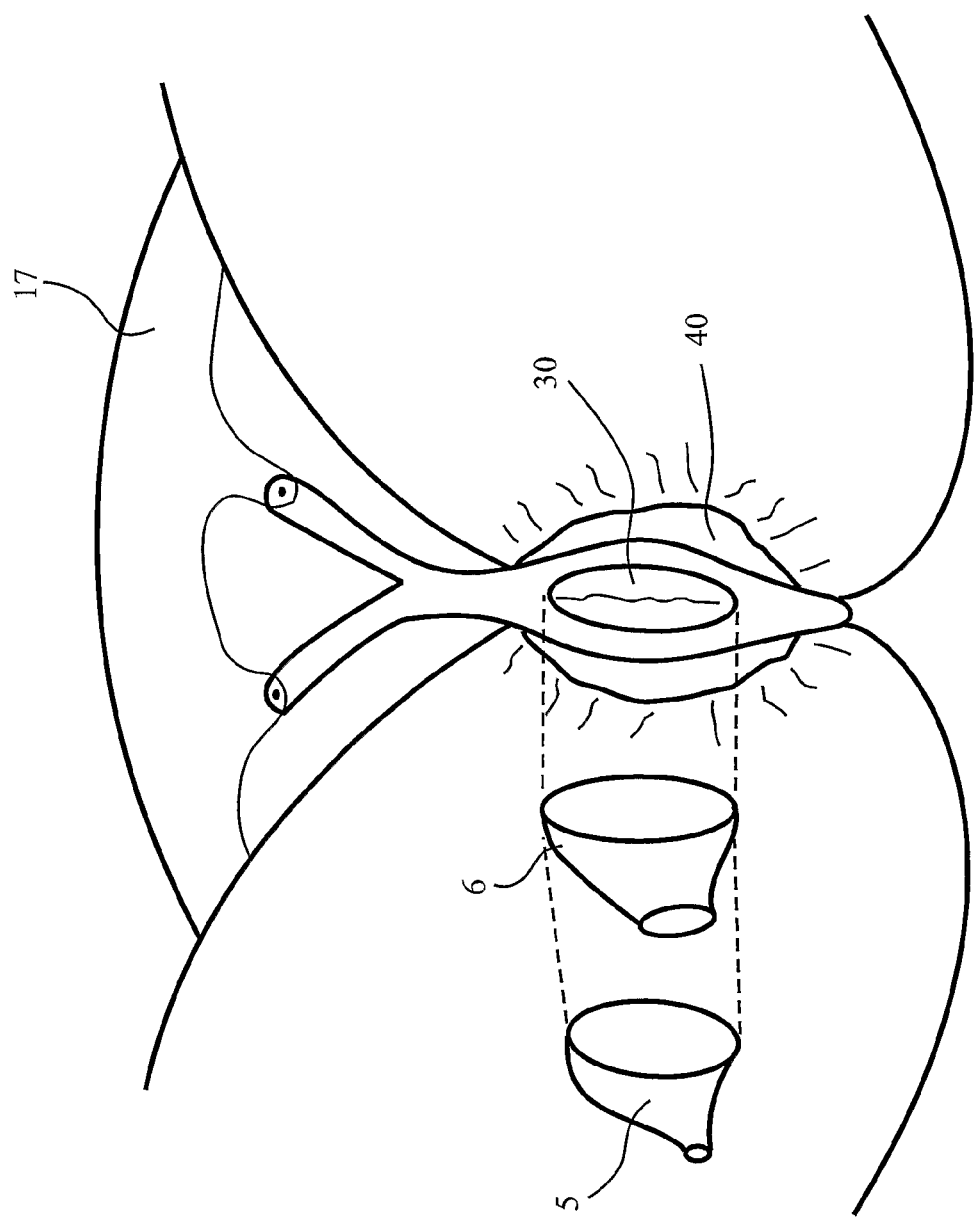
FIG. 5 is an exploded schematic view of the device and support harness as worn by a user.
Figure 6:
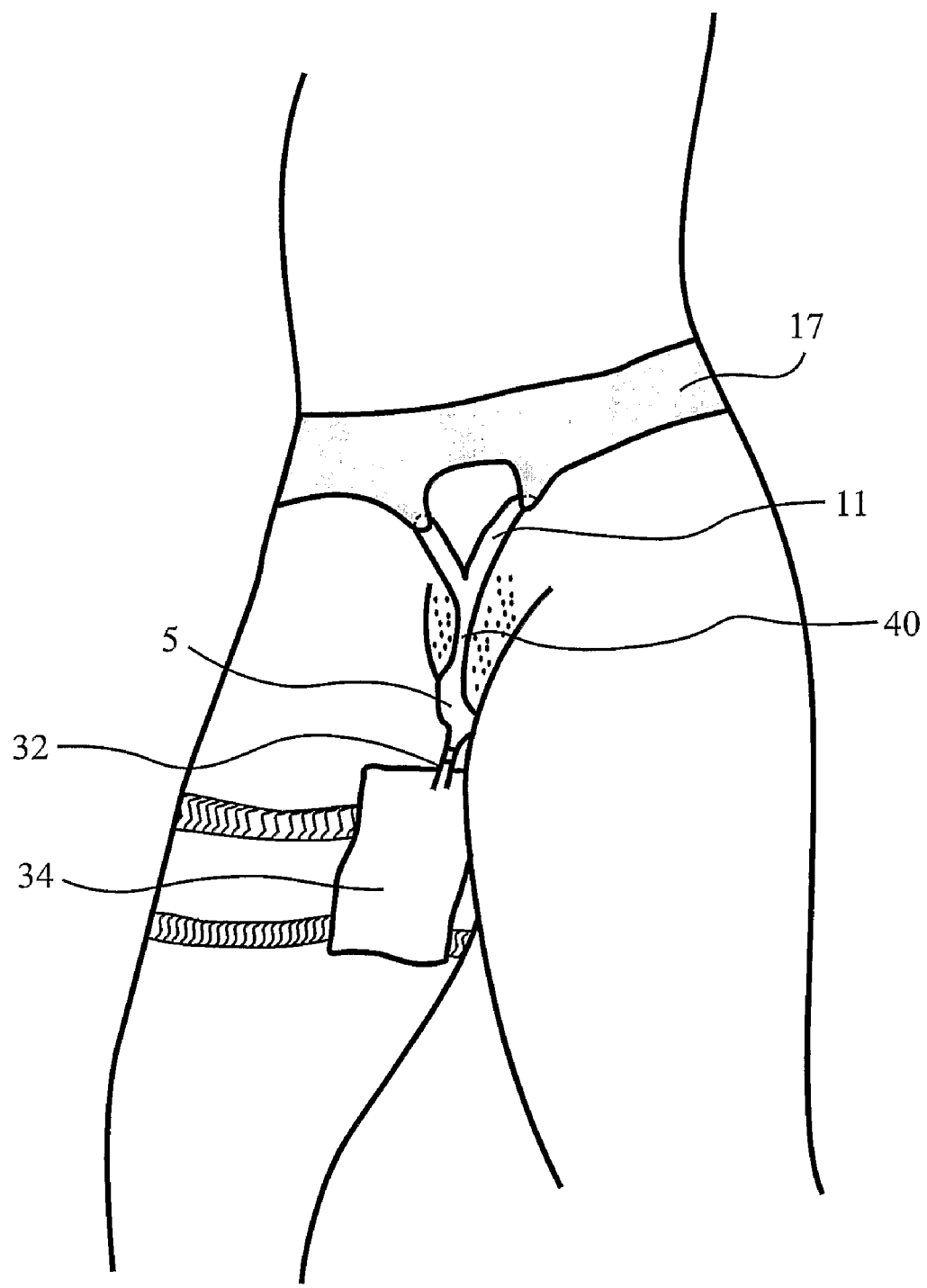
FIG. 6 shows a device worn by the user and urine collection means.

Referring to FIGS. 5 and 6, in use the device stretch fitted so that the labia minora 30 of the patient passes through the opening 3 in the strip portion and through the opening of the interior wall. When the strip portion is relaxed the base of the labia minora is surrounded by the opening in the strip portion. The labia minora lodge in the interior wall 6 of the cup. The anterior and posterior support straps are then engaged with the corresponding support straps on the harness so as to provide sufficient tension to maintain the flat upper surface of the flexible strip against the flesh surrounding the labia minora. Multiple attachment points are provided so that an optimum tension may be achieved for any user and ensure fluid tight seal is maintained at all times. An effective continuous seal can be maintained from the pubis to beyond the anus. Urine or other fluid exiting through the labia minora passes through the opening 9 of the interior wall and into the cavity 24. The fluid will then drain from the cavity through opening 8 of the exterior wall which is connected via a tube 32 to a collection bag 34. Any fluid not draining through the exit 8 is retained in the cavity 24 and is prevented form draining back through the opening 9 of the inner wall both by the spacing apart of the inner and outer walls and the shaping of the inner wall.

The invention claimed is:

1. A non-intrusive female urinary incontinence device (13) comprising a flexible elastic substantially flat strip (1) having a flat upper face and a lower face, an opening (3) being provided in the strip communicating between the upper and lower faces, a fluid collection means surrounding (4) the opening in a fluid tight manner on the lower face of the strip and means (19) for attaching the device to a supporting means (17), wherein the strip and opening are sized and shaped such that when it is stretch fitted over the external urogenital organs, the labia minora extends through the opening and the strip terminates against flesh residing outside the labia minora and inside the labia majora without any intervening material and wherein the flat upper face of the strip conforms to the shape of the wearer and defines a fluid tight fit between the upper face of the strip and the flesh surrounding the labia minora and around the base of the labia minora, such that, in use, urine is conveyed from the urethra, through the labia minora, into the collection means without leakage.

2. A device according to claim 1 wherein the fluid collection device comprises a funnel portion the curved wall of which at an upper end extends circumferentially from the surface of the oval region around the opening and curves inwards to a lower open end (8) suitable for communicating with a collection vessel (34).

3. A device according to claim 2 wherein the anterior surface of the wall of said funnel curves more sharply than the posterior surface, such that the lower opening (8) at the base of the funnel lies in a lower plane than that of the opening (3) in the strip.

4. A device according to claim 1 wherein said funnel has a double-walled structure, the inner curved wall (5) narrowing symmetrically and more sharply than the outer wall so that an internal opening (9) is formed substantially parallel to and of smaller radius than the opening (3) in the strip.

5. A device according to claim 3 wherein a cavity (24) is formed between the posterior surface of the inner wall and the posterior surface of the outer wall such that, when the user is in a horizontal position, urine which has passed through the internal opening (9) of the funnel is prevented from flowing back into the cavity between said opening and the oval opening of the strip.

6. A device according to claims 3 wherein the inner wall (5) and outer wall (6) are spaced apart such that urine in the cavity (24) is prevented from flowing back into the interior opening (9).

7. A device according to claim I wherein the exterior wall (6) of the funnel is constructed of resilient flexible material and the interior wall (5) is constructed with substantially the same material as the strip.

8. A device according to claim 1 wherein the funnel is integral to the strip.

9. A device according to claims 1 wherein said strip comprises divergent elongated straps at the front and rear to provide anterior and posterior support straps for attachment to a supporting waistband, so that in use the strip is stretched tightly over the external urogenital organs.

10. A device according to claim 9 wherein the length of said straps is adjustable with respect to the waistband to allow for differences in size and shape of the user.

11. A device according to claim 1 in which the strip portion is maintained under tension in use.

12. A urinary incontinence device further comprising a waistband (13) and means (20) for attachment to the device of claim 1.

13. A urinary incontinence device according claim 12 wherein the attachment means is adjustable to maintain a positive tension on the device when in use.

14. A urinary incontinence device according to claim 1, wherein the fluid collection means comprises a downwardly extending funnel that is sized and configured to engage the strip and reside inside folds of the labia majora allowing a wearer to place underwear over the funnel.

15. A urinary incontinence device according to claim 1, wherein the strip elongates anteriorly and posteriorly to merge into extension straps thereby providing a continuous seal.

16. A female urinary incontinence device, comprising:
an elastic strip having two opposing outer perimeter segments surrounding a urine flow passage, the outer perimeter segments sized and configured to stretch and reside snugly against flesh at a base region of a wearer's labia minora and within inner tissue folds of the wearer's labia majora so that the strip directly contacts without any intervening material flesh surrounding the base of the labia minora to define a fluid-tight seal while allowing the labia minora to extend through the urine flow passage of the strip;
a collection funnel sealably attached to the strip and in fluid communication with the urine flow passage of the strip; and
a securing member configured to hold the strip in position on the wearer, wherein, in use, urine flows from the urethra, between the labia minora, then to the funnel in a leak-proof manner.

17. A device according to claim 16, wherein the strip is a flat flexible elastic strip of silicone.

18. A female fluid collection device, comprising:
an elastic strip having two opposing outer perimeter segments surrounding a flow passage, the outer perimeter segments sized and configured to stretch and reside snugly against tissue surrounding a base region of a wearer's labia minora but within inner tissue folds of the wearer's labia majora without any intervening material so that the strip directly contacts tissue surrounding the base of the labia minora to define a fluid-tight seal with the labia minora extending through the flow passage of the strip;
a collection funnel sealably attached to the strip and in fluid communication with the flow passage of the flat elastic strip; and
a securing member configured to hold the strip in position on the wearer.
wherein, in use, fluid flows from the body between the labia minora, then to the funnel in a leak-proof manner.

19. A device according to claim 18, wherein the strip is a flexible flat elastic silicone strip.

\* \* \* \* \*